US011045643B2

(12) United States Patent
Fischer et al.

(10) Patent No.: US 11,045,643 B2
(45) Date of Patent: Jun. 29, 2021

(54) SINGLE-SITE IMPLANTATION METHODS FOR MEDICAL DEVICES HAVING MULTIPLE LEADS

(71) Applicant: PACESETTER, INC., Sylmar, CA (US)

(72) Inventors: Avi Fischer, Los Angeles, CA (US); Xiaoyi Min, Simi Valley, CA (US); Kyungmoo Ryu, Palmdale, CA (US); Gene A. Bornzin, Simi Valley, CA (US); Keith Victorine, Santa Clarita, CA (US); Stuart Rosenberg, Castaic, CA (US); Shubha Asopa, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 483 days.

(21) Appl. No.: 15/973,249

(22) Filed: May 7, 2018

(65) Prior Publication Data

US 2019/0336747 A1    Nov. 7, 2019

(51) Int. Cl.
*A61N 1/05*     (2006.01)
*A61B 17/34*    (2006.01)
*A61N 1/39*     (2006.01)

(52) U.S. Cl.
CPC ........ *A61N 1/0504* (2013.01); *A61B 17/3468* (2013.01); *A61N 1/39622* (2017.08)

(58) Field of Classification Search
CPC .......................... A61N 1/0504; A61N 1/39622
USPC ........................................................ 606/129
See application file for complete search history.

(56) References Cited

U.S. PATENT DOCUMENTS

| | | |
|---|---|---|
| 6,866,044 B2 | 3/2005 | Bardy et al. |
| 7,149,575 B2 | 12/2006 | Ostroff et al. |
| 7,536,222 B2 | 5/2009 | Bardy et al. |
| 7,655,014 B2 | 2/2010 | Ko et al. |
| 7,774,059 B2 | 8/2010 | Ostroff et al. |
| 8,831,720 B2 | 9/2014 | Bardy et al. |
| 9,295,834 B2 | 3/2016 | Wulfman et al. |

(Continued)

OTHER PUBLICATIONS

De Maria et al.; "The Entirely Subcutaneous Defibrillator (S-ICD): State of the Art and Selection of the Ideal Candidate" Current Cardiology Reviews; 2015; 7 pages.

(Continued)

*Primary Examiner* — Nadia A Mahmood
(74) *Attorney, Agent, or Firm* — The Small Patent Law Group LLC; Dean D. Small

(57) ABSTRACT

Methods and devices include making an incision at a single site of a patient. The single site located at an anterior of a chest or abdomen. The method also includes inserting a tunneling tool through the incision at the single site and preparing a first tunnel to a subcutaneous posterior location. A path of the first tunnel at least one of i) extends over a plurality of Intercostal gaps of the chest or ii) extends along and within one of the intercostal gaps. The method also includes positioning a first lead having an electrode within the first tunnel and preparing a second tunnel to a subcutaneous parasternal location along the chest. The method also includes positioning a second lead having an electrode within the second tunnel and positioning a pulse generator within a subcutaneous pocket and operatively coupling the first and second leads to the pulse generator.

23 Claims, 9 Drawing Sheets

(56) References Cited

U.S. PATENT DOCUMENTS

2002/0049475 A1* 4/2002 Bardy .................. A61N 1/375
607/5
2016/0121130 A1 5/2016 Cinbis et al.

OTHER PUBLICATIONS

Kempa et al.; "Implantation of additional Subcutaneous Array Electrode Reduces Defibrillation Threshold in ICD Patients—Preliminary Results" Archives of Medical Science: AMS; 2012; 5 pages.

* cited by examiner

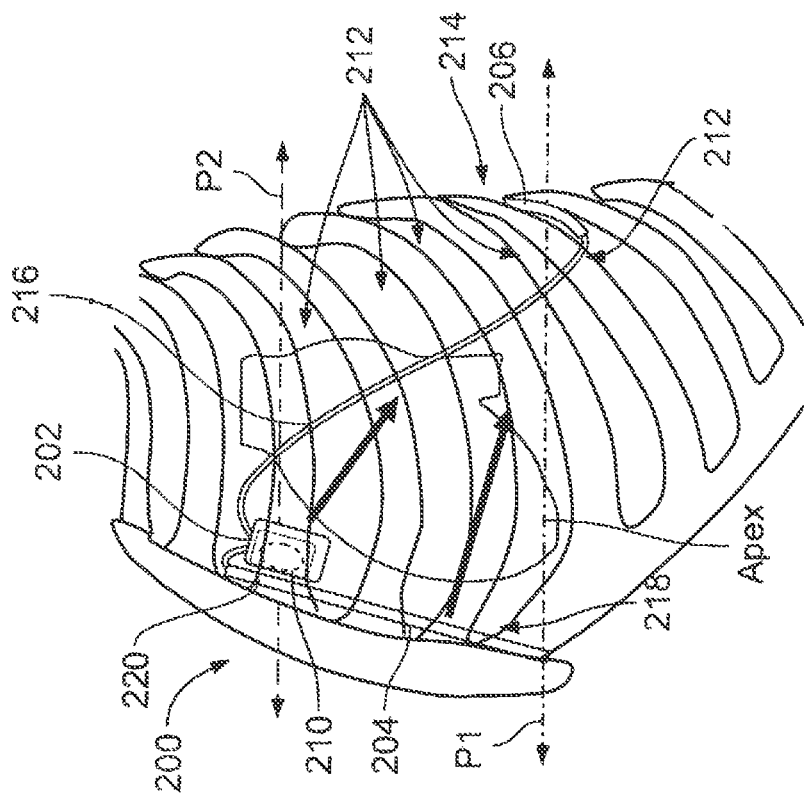
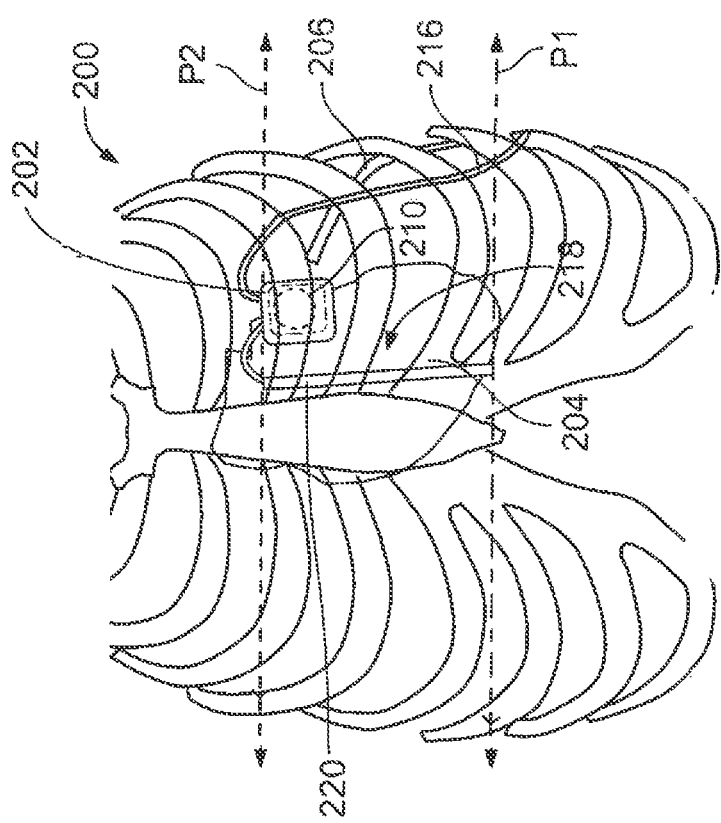

SINGLE-SITE IMPLANTATION METHODS FOR MEDICAL DEVICES HAVING MULTIPLE LEADS

BACKGROUND

Embodiments of the present disclosure relate generally to implantable medical devices and methods, and more particularly to medical devices having pulse generators and multiple implanted leads.

Currently, implantable medical devices (IMD) are provided for a variety of cardiac applications. IMDs may include a "housing" or "canister" (or "can") and one or more electrically-conductive leads that connect to the housing through an electro mechanical connection. IMDs contain electronics (e.g., a power source, microprocessor, capacitors, etc.) that control electrical activation of the leads to provide various functionalities. For instance, current IMDs may be configured for pacemaking, cardioversion, and/or defibrillation.

An implantable cardioverter-defibrillator (ICD) is one such medical device and it is designed to monitor heart rate, recognize certain events (e.g., ventricular fibrillation or ventricular tachycardia), and deliver electrical shock to reduce the risk of sudden cardiac death from these events. An ICD typically includes a pulse generator that is contained within a housing and one or more electrically-conductive leads that are controlled by the pulse generator. One conventional type of ICD uses transvenous leads in the right ventricle for detection and treatment of tachyarrhythmia. Although transvenous ICDs (or TV-ICDs) can prevent sudden cardiac death, TV-ICDs have certain drawbacks. For instance, obtaining venous access can be difficult and time-consuming, thereby prolonging the medical procedure. TV-ICDs are also associated with undesirable conditions or events, such as hemopericardium, hemothorax, pneumothorax, lead dislodgement, lead malfunction, device-related infection, and venous occlusion.

A second type of ICD, referred to as a subcutaneous ICD (or S-ICD), uses an electrode configuration that can reside entirely within the subcutaneous space. Unlike the transvenous types, the S-ICDs lack intravenous and intracardiac leads and, as such, can be less likely to have the undesirable conditions or events associated with TV-ICDs. The S-ICD typically includes a shock coil that extends parallel to the sternum in a pectoral region of the patient. The shock coil is flanked by two sensing electrodes. The sensing electrodes sense the cardiac rhythm and the shock coil delivers countershocks through the subcutaneous tissue of the chest wall.

The conventional S-ICD is implanted using three separate incisions: an axilla incision, an inferior parasternal incision near the xiphoid process, and a superior parasternal incision. More specifically, the pulse generator is positioned in a pocket of the axilla that is accessed through the axilla incision. The lead is implanted using the pocket and the two parasternal incisions. Like the TV-ICD, conventional S-ICDs have been effective in reducing the incidence of sudden cardiac death. However, the risk of infection or other complication increases with each incision. Accordingly, a need remains for an implantation method requiring fewer incisions while also providing an S-ICD configuration that may deliver a sufficient amount of energy for defibrillation.

SUMMARY

Embodiments set forth herein include implantable medical devices (SIMDs), systems that include SIMD, and methods of using and positioning the same. IMDs may include a pulse generator and multiple leads in which at least two leads are implanted through a single incision site. The leads may have one or more electrode segments. In some embodiments, the entire SIMD may be positioned subcutaneously (e.g., beneath the skin but above layers of skeletal muscle tissue, rib bones, and costal cartilage). In some embodiments, only designated elements of the SIMD are positioned subcutaneously. In other embodiments, at least some elements of the SIMD may be positioned submuscularly. For example, the pulse generator may be implanted submuscularly (e.g., under the serratus anterior muscle) or under the serratus anterior fascia but above muscle.

In accordance with embodiments herein, a method is provided that includes making an incision at a single site of a patient. The single site located at an anterior of a chest or abdomen of the patient. The method also includes Inserting a tunneling tool through the incision at the single site and preparing a first tunnel from the single site to a subcutaneous posterior location. A path of the first tunnel at least one of i) extends over a plurality of intercostal gaps of the chest or ii) extends along and within one of the intercostal gaps. The method also includes positioning a first lead having an electrode within the first tunnel and inserting the tunneling tool or a different tunneling tool through the incision at the single site and preparing a second tunnel from the single site to a subcutaneous parasternal location along the chest. The method also includes positioning a second lead having an electrode within the second tunnel and positioning a pulse generator within a subcutaneous pocket and operatively coupling the first and second leads to the pulse generator.

In some aspects, the path of the first tunnel extends beyond a posterior axillary line of the patient. The single site is the only site where an incision is made for positioning the first lead, for positioning the second lead, and for positioning the pulse generator. Optionally, the posterior location is within a region below the inferior angle of a scapula.

In some aspects, the method further comprises shaping the tunneling tool or the other tunneling tool based on an anatomical shape of the patient along the corresponding path.

In some aspects, the tunneling tool is surrounded by a removable sheath, wherein preparing the first tunnel includes moving the tunneling tool and the removable sheath through subcutaneous tissue to form the first tunnel and removing the tunneling tool such that the removable sheath remains within the first tunnel.

In some aspects, at least one of the first lead or the second lead is anchored to the deep fascia within the subcutaneous pocket at an anchor point. The anchor point is the only anchor point in which the at least one lead is anchored directly to patient.

In some aspects, a volume of the pulse generator is at most 40 milliliters.

In some aspects, the pulse generator is configured to generate a defibrillating energy of at most 50 Joules. The pulse generator and the electrode of the second lead have a common polarity.

In some aspects, the electrode of the first lead has an active length that is at least 12 centimeters (cm), and the electrode of the second lead has an active length that is at least 8 cm.

In some aspects, the electrode of the first lead includes an electrode patch positioned at the posterior location. The electrode patch has an active area that is at least 30 $cm^2$.

In accordance with one or more embodiments herein, a method is provided that includes making an incision at a single site of a patient. The single site is located at an anterior of a chest of the patient. The method also includes inserting a first tunneling tool through the incision at the single site. The tunneling tool has an elongated shaft and a removable sheath that surrounds the elongated shaft. The method also includes displacing underlying tissue with the tunneling tool along a designated path to prepare a first tunnel. The first tunnel extends from the single site, over a plurality of intercostal gaps of the chest, and within one of intercostal gaps to a subcutaneous posterior location. The method also includes withdrawing the elongated shaft. The removable sheath maintains the first tunnel. The method also includes positioning a first lead having an electrode within the first tunnel and withdrawing the removable sheath. The method also includes inserting a second tunneling tool through the incision at the single site. The second tunneling tool has an elongated shaft and a removable sheath that surrounds the elongated shaft of the second tunneling tool. The method also includes displacing underlying tissue with the second tunneling tool along a designated path to prepare a second tunnel. The second tunnel extends from the single site to a subcutaneous parasternal location. The method also includes withdrawing the elongated shaft of the second tunneling tool. The removable sheath of the second tunneling tool maintains the second tunnel. The method also includes positioning a second lead having an electrode within the second tunnel and withdrawing the removable sheath of the second tunneling tool. The method also includes forming a subcutaneous pre-pectoral pocket. The method also includes positioning a pulse generator within the subcutaneous pre-pectoral pocket and operatively coupling the first and second leads to the pulse generator.

In some aspects, the path of the first tunnel extends beyond a posterior axillary line of the patient. The single site is the only site where an incision is made for positioning the first lead, for positioning the second lead, and for positioning the pulse generator.

In some aspects, the method also includes shaping at least one of the elongated shafts based on an anatomical shape of the patient along the corresponding designated path.

In some aspects, the pulse generator is configured to generate a defibrillating energy of at most 50 Joules. The pulse generator and the electrode of the second lead have a common polarity.

In some aspects, the first lead has an electrode with an active length that is at least 12 centimeters (cm). The second lead has an electrode with an active length that is at least 8 cm.

In accordance with one or more embodiments, a method is provided that includes making an incision at a single site of a patient. The single site is located at an abdomen of the patient. The method also includes inserting a first tunneling tool through the incision at the single site. The first tunneling tool having an elongated shaft and a removable sheath that surrounds the elongated shaft. The method also includes displacing underlying tissue with the first tunneling tool along a designated path to prepare a first tunnel. The first tunnel extends from the single site along an intercostal gap to a subcutaneous posterior location. The method also includes withdrawing the elongated shaft. The removable sheath maintains the first tunnel. The method also includes positioning a first lead having an electrode within the first tunnel and withdrawing the removable sheath. The method also includes inserting a second tunneling tool through the incision at the single site. The second tunneling tool has an elongated shaft and a removable sheath that surrounds the elongated shaft of the second tunneling tool. The method also includes displacing underlying tissue with the second tunneling tool along a designated path to prepare a second tunnel. The second tunnel extends in a superior direction from the single site to a subcutaneous parasternal location. The method also includes withdrawing the elongated shaft of the second tunneling tool. The removable sheath of the second tunneling tool maintains the second tunnel. The method also includes positioning a second lead having an electrode within the second tunnel. The method also includes withdrawing the removable sheath of the second tunneling tool and forming a subcutaneous abdominal pocket. The method also includes positioning a pulse generator within the abdominal pre-pectoral pocket and operatively coupling the first and second leads to the pulse generator.

In some aspects, the path of the first tunnel extends beyond a posterior axillary line of the patient. The single site is the only site where an incision is made for positioning the first lead, for positioning the second lead, and for positioning the pulse generator.

In some aspects, the method also includes shaping at least one of the elongated shafts based on an anatomical shape of the patient along the corresponding designated path.

In some aspects, the pulse generator is configured to generate a defibrillating energy of at most 50 Joules. The pulse generator and the electrode of the second lead have a common polarity.

In some aspects, the electrode of the first lead includes a patch electrode.

BRIEF DESCRIPTION OF THE DRAWINGS

FIG. 8 is anterior view of a human thoracic cage that illustrates relative positions of a pulse generator within a pectoral region, a parasternal electrode, and a posterior electrode.

FIG. 9 is a lateral view of the thoracic cage of FIG. 8 illustrating the relative positions of the pulse generator, the parasternal electrode, and the posterior electrode coil.

DETAILED DESCRIPTION

Figure 1:
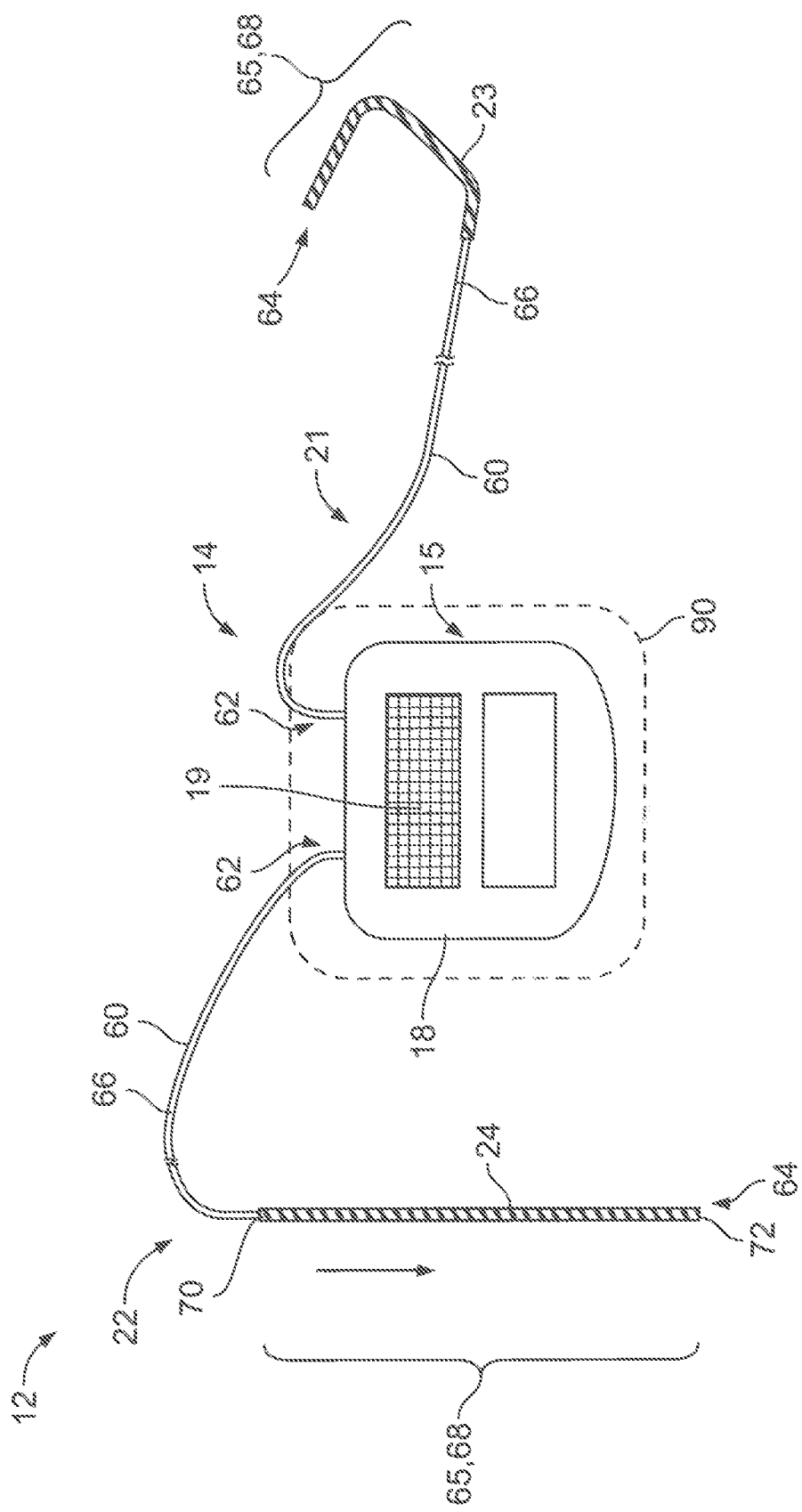
FIG. 1 is a schematic representation of an implantable medical system in accordance with an embodiment.

Embodiments set forth herein include implantable medical devices (SIMDs), systems that include SIMD, and methods of using and positioning the same. In certain embodiments, the SIMD is a subcutaneous implantable cardioverter-defibrillator (S-ICD) in which only one single incision site is used to position the first lead, the second lead, and the pulse generator. The pulse generator is positioned within a pocket that is accessed through the single incision site, and the first and second leads are positioned within tunnels that extend from the single incision site (or pocket). Particular embodiments include a pulse generator that is positioned within a pectoral region of a chest of a patient or within an abdominal region of the patient. In other embodiments, the SIMD is an implantable cardioverter-defibrillator (S-ICD) in which only one single incision site is used to position the first lead, the second lead, and the pulse generator, wherein the pulse generator is position submuscularly.

As used herein, the term "subcutaneously," when used to describe implanting a device (e.g., pulse generator, lead body, electrode, etc.), means implanting the device beneath the skin but above layers of skeletal muscle tissue, rib bones, and costal cartilage. The device is typically positioned under or partially within the subcutaneous tissue. When the term "subcutaneous" is used to characterize the entire implantable medical system, the term means that most of the operating components of the system (e.g., the pulse generator, shocking electrodes, optional sensing electrodes, lead bodies) or each and every one of the operating components is beneath the skin, but above layers of skeletal muscle tissue, rib bones, and costal cartilage. Compared to transvenous ICD implantation, subcutaneous implantation may be less complex, less invasive, and less time-consuming.

An electrode represents an electrically conductive portion of the lead that is operable to deliver energy for antiarrhythmic therapy. Embodiments include an electrode configuration that includes at least three shock electrodes. A shock electrode may be, for example, a coil electrode, a ring electrode, a patch electrode, or the like. Each of the leads includes at least one electrode, and the pulse generator may include another electrode. As used herein, a pulse generator or a housing of the pulse generator "includes an electrode" when the housing forms or constitutes the electrode or when the housing (or other part of the pulse generator) has a discrete electrode attached thereto. Optionally, the electrode configuration may include additional sensing electrodes. Illustrated embodiments include a parasternal coil electrode and a posterior electrode (e.g., coil electrode or patch electrode) that is positioned below the inferior angle of a scapula. It is contemplated, however, that different types of electrodes may be used in these locations.

A lead typically includes a lead body having an elongated flexible tube or sleeve comprising, for example, a biocompatible material (e.g., polyurethane, silicone, etc.). The lead body may include a single lumen (or passage) or multiple lumen (or passages) within the flexible tube. A lead may have multiple electrical conductors (not shown) that electrically couple the electrode(s) of the lead to the pulse generator. The electrical conductors may be cabled conductors coated with PTFE (poly-tetrafluoroethylene) and/or ETFE (ethylenetetrafluoroethylene). The electrical conductors are terminated to the respective electrode. The lead body may be configured for receiving a guide wire or stylet that enable positioning of the lead.

Electrode configurations may reliably provide a sufficient amount of energy for antiarrhythmic therapy (e.g., defibrillation). Embodiments may enable pulse generators with defibrillation thresholds (DFTs) that are less than known systems. For example, the DFT in some embodiments may be at most 50 Joules. The DFT in certain embodiments may be at most 45 Joules or, more particularly, at most 40 Joules. Embodiments may also enable using pulse generators or canisters with a smaller volume than known systems. For instance, a volume of the pulse generator may be at most 40 milliliters or at most 35 milliliters.

Furthermore, the features, structures, or characteristics described herein may be combined in any suitable manner in one or more embodiments. In this description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The description is intended only by way of example, and simply illustrates certain example embodiments, FIG. 1 illustrates a graphical representation of an implantable medical system 12 that is configured to apply therapy to a heart (not shown). In particular embodiments, the system 12 may apply pacing therapy, cardiac resynchronization therapy (CRT), and general arrhythmia therapy, including defibrillation. The system 12 includes a subcutaneous implantable medical device (SMD) 14 that is configured to be implanted in a subcutaneous area exterior to the heart. The SIMD 14 is positioned in a subcutaneous pocket 90. The system 12 also includes a first lead 21 having an electrode 23 and a second lead 22 having an electrode 24 that are configured for defibrillation. Optionally, each of the first and second leads 21, 22 may include one or more additional electrodes (e.g., sensing electrodes).

The pulse generator 15 may be implanted subcutaneously and at least a portion of the first and second leads 21, 22 may be implanted subcutaneously, in particular embodiments, the SIMD 14 is an entirely or fully subcutaneous SIMD. In FIG. 1, the SIMD 14 is positioned within a pectoral region. Optionally, the SIMD 14 may be positioned in a different subcutaneous region. The SIMD 14 may be configured to detect or sense cardiac activity (e.g., cardiac rhythm). The SIMD 14 is configured to deliver various arrhythmia therapies, such as defibrillation therapy, pacing therapy, anti-tachycardia pacing therapy, cardioversion therapy, and the like based on the cardiac activity.

The pulse generator 15 includes a housing or canister 18. The pulse generator 15 also includes a pulse-generator (PG) electrode 19. The pulse generator 15 or the housing 18 include an electrode when the housing 18 forms or constitutes the electrode or when the housing 18 (or other part of the pulse generator 15) has a discrete electrode attached thereto. In particular embodiments, the housing 18 forms the PG electrode 19. In other embodiments, as shown in FIG. 1, the PG electrode 19 is a discrete electrode attached to the housing 18.

Each of the first and second leads 21, 22 includes an elongated lead body 60 that extends from a PG-end portion 62 to a distal tip 64. The PG-end portion 62 is operably connected to the pulse generator 15. The PG-end portion 62 may include one or more electrodes (not shown) that electrically engage respective terminals (not shown) of the pulse generator 15. More specifically, the PG end portion 62 may be inserted into a port of the pulse generator 15 where the terminals are located.

The elongated lead body 60 includes an elongated flexible tube or sleeve 66 comprising, for example, a biocompatible material (e.g., polyurethane, silicone, etc.). The lead body 60 may include a single lumen (or passage) or multiple lumen (or passages) within the flexible tube 66. Each of the first and second leads 21, 22 may also include a plurality of electrical conductors (not shown) that electrically couple the shocking electrode (and optionally sensing electrodes) to the pulse generator 15. The electrical conductors may be cabled conductors coated with PTFE (poly-tetrafluoroethylene) and/or ETFE (ethylenetetrafluoroethylene). The lead body 60 may be configured for receiving a stylet that enable positioning of the lead. The electrical conductors are terminated to the respective electrodes. For example, the conductors may be terminated to an electrode (not shown) near the PG end portion 62 and a respective electrode (e.g., electrode 23 or electrode 24) along a distal segment 65 that extends to and includes the distal tip 64.

In the illustrated embodiment, each of the electrodes 23, 24 is a single coil electrode. In other embodiments, however, the electrode 23 and/or the electrode 24 may include multiple different electrodes. In other embodiments, the electrode 23 and/or the electrode 24 may include a patch electrode. The electrodes 23, 24 have respective active lengths. An active length 68 represents a length of the electrode (e.g., a coil electrode) that may be used to provide electrical energy. The active length 68 is measured between a proximal end 70 and a distal end 72. For embodiments that include patch electrodes, the patch electrode may include an active area that may be used to provide the electrical energy.

In some embodiments, the active length of the parasternal electrode 24 is at least five (5) cm. In some embodiments, the active length of the parasternal electrode 24 may be at least seven (7) cm or, more particularly, at least nine (9) cm, in certain embodiments, the active length of the parasternal electrode 24 may be at least ten (10) cm or, more particularly, at least fifteen (15) cm.

In some embodiments, the active length of the posterior electrode 23 is at least ten (10) centimeters (cm). In some embodiments, the active length of the posterior electrode 23 may be at least twelve (12) cm or, more particularly, at least fifteen (15) cm. In certain embodiments, the active length of the posterior electrode 23 may be at least seventeen (17) cm or, more particularly, at least 20 cm. A maximum active length may be, for example, about 30 cm.

For embodiments, in which the posterior electrode 23 is a patch electrode, the patch electrode has an active area based on an active width and active length of the patch electrode. An active width of the electrode is measured perpendicular to the active length from an outer edge of the electrode to an opposite outer edge of the electrode. It should be understood that the patch electrode may include an array of individual electrodes. The active width of the patch electrode may be at least four (4) cm and an active length of the patch electrode may be at least 5 (cm). An active area (length times width) may be at least 30 cm$^2$ or, more particularly, at least 40 cm$^2$. Examples of the active width and active length (w×l) include 3×6, 3×7, 3×8, 4×6, 4×7, 4×8, 5×6, 5×7, 5×8. The active area may be, for example, at least 15 cm$^2$, at least 18 cm$^2$, at least 20 cm$^2$, at least 25 cm$^2$, at least 30 cm$^2$, or at least 40 cm$^2$. It should be understood, however, that the active area of a patch electrode is not necessarily rectangular and may have other shapes.

The electrodes 23, 24 may be positioned subcutaneously at a level that is suitable for providing a sufficient amount of energy for defibrillation. For example, the electrode 23 may be positioned subcutaneously at a level that approximately aligns with an apex of a heart of the patient. At least a portion of the electrode 23 may be positioned at or below an apex of the heart. For example, the electrode 23 may be positioned along an intercostal gap between the seventh and eighth ribs of the patient or along an intercostal gap between the sixth and seventh ribs of the patient. The electrode 23 may be positioned below the inferior angle of a scapula. It is contemplated, however, that the electrode 23 may be positioned at other levels with respect to the heart.

The electrode 24 may be positioned subcutaneously an extend parallel to a sternum of a patient (or a parasternal lime of the sternum). The electrode 24 may be spaced apart from the sternum by, for example, one to three centimeters. Although a typical location for the electrode 24 may be on a left side of the sternum, it is possible that the electrode 24 may be positioned along a right side of the sternum. It is contemplated, however, that the electrode 24 may be positioned at other levels with respect to the heart.

As described herein, for some embodiments, the subcutaneous pocket 90 is a pre-pectoral pocket located in the pectoral region. In other embodiments, however, the subcutaneous pocket 90 is an abdominal pocket located in the pectoral region. The shock vectors may be configured accordingly using a PG electrode of the pulse generator, the parasternal electrode 24, and the posterior electrode 23. In some embodiments, the electrical energy is generated by the PG electrode and the parasternal electrode and is directed to the posterior electrode.

Figure 2:
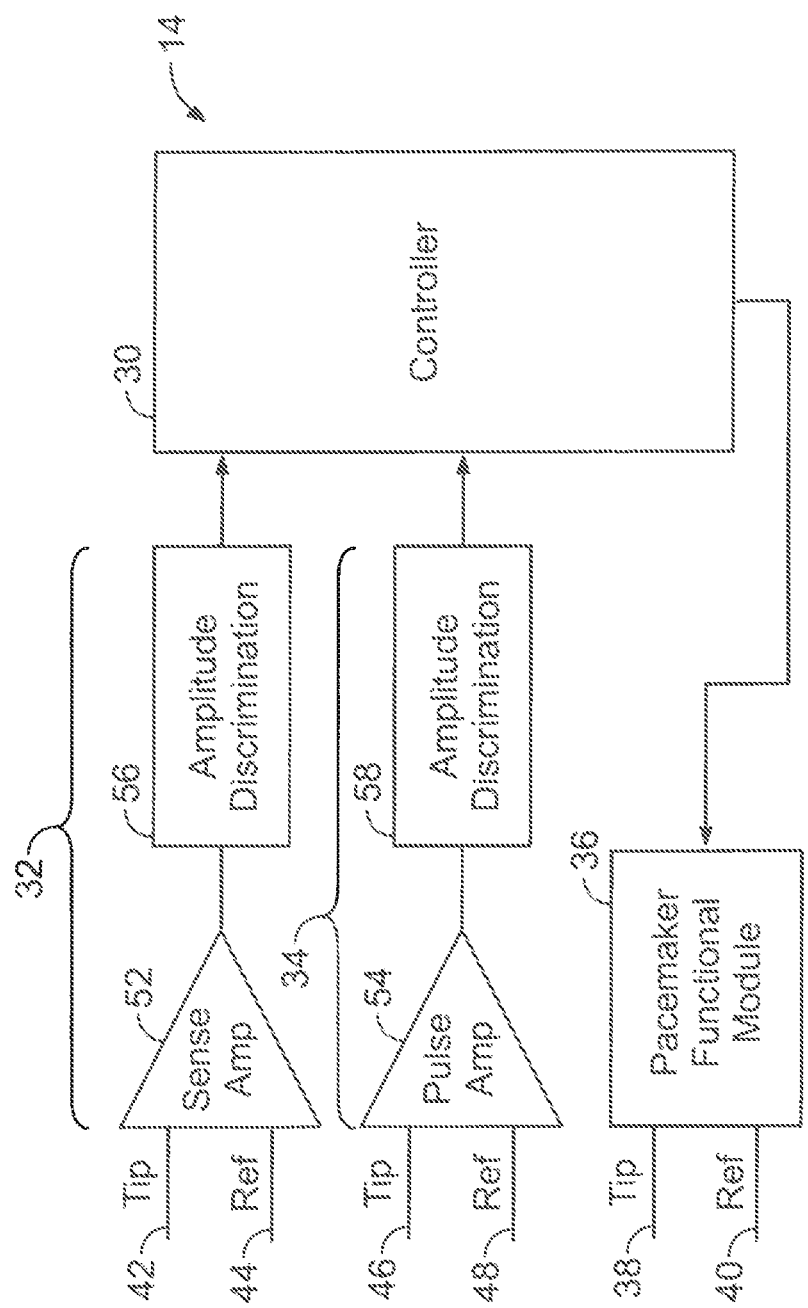
FIG. 2 illustrates a block diagram of at least a portion of the circuitry within a subcutaneous implantable medical device (SIMD) in accordance with an embodiment herein that may be used with the system of FIG. 1.

FIG. 2 illustrates a simple block diagram of at least a portion of the circuitry within the SIMD 14. The SIMD 14 includes a controller 30 that may be coupled to cardiac sensing circuitry 32 and pulse sensing circuitry 34. The controller 30 also utilizes or communicates with various other electronic components, firmware, software, and the like that generally perform sensing and pacing functions (as generally denoted by a pacemaker functional block 36). While the examples herein are provided for pacing and defibrillation functions, the SIMD could be programmed to perform anti-tachycardia pacing, cardiac rhythm therapy, and the like. The cardiac sensing circuitry 32 is configured to detect one or more cardiac events (e.g., ventricular fibrillation, ventricular tachycardia, or other arrhythmia). The pulse sensing circuitry 34 is configured to detect event markers.

The controller 30 is configured to analyze incoming paced cardiac events (as sensed over the cardiac sensing circuitry 32). Based on this analysis, the controller 30 in the SIMD 14 may perform various pacemaker related actions, such as setting or ending timers, recording data, delivery of therapy, and the like. The controller 30 of the SIMD 14 may also perform various cardioversion/defibrillation related functions. In the example of FIG. 2, outputs 38 and 40 represent output terminals that are coupled through a switching circuit (in the functional module 36) to corresponding electrodes on the housing of the SIMD 14. Alternatively, the outputs 38 and 40 may be coupled to respective electrode on along the leads 21, 22 (FIG. 1).

Inputs 42-48 are provided to the cardiac sensing circuitry 32 and pulse sensing circuitry 34. By way of example, with reference to SIMD 14, inputs 42 and 44 may be coupled to sensing electrodes that supply sensed signals to a sensing amplifier 52. Inputs 46 and 48 may be coupled to the same or different sensing electrodes to provide sensed signals to a pulse amplifier 54. An output of the sensing amplifier 52 is supplied to amplitude discriminator 56, while an output of the pulse amplifier 54 is supplied to amplitude discriminator 58. Outputs of the amplitude discriminators 56 and 58 are then provided to the controller 30 for subsequent analysis and appropriate actions. The inputs 42 and 44 may be coupled to various combinations of the electrode 23, 24 or the PG electrode 19.

Figure 3:
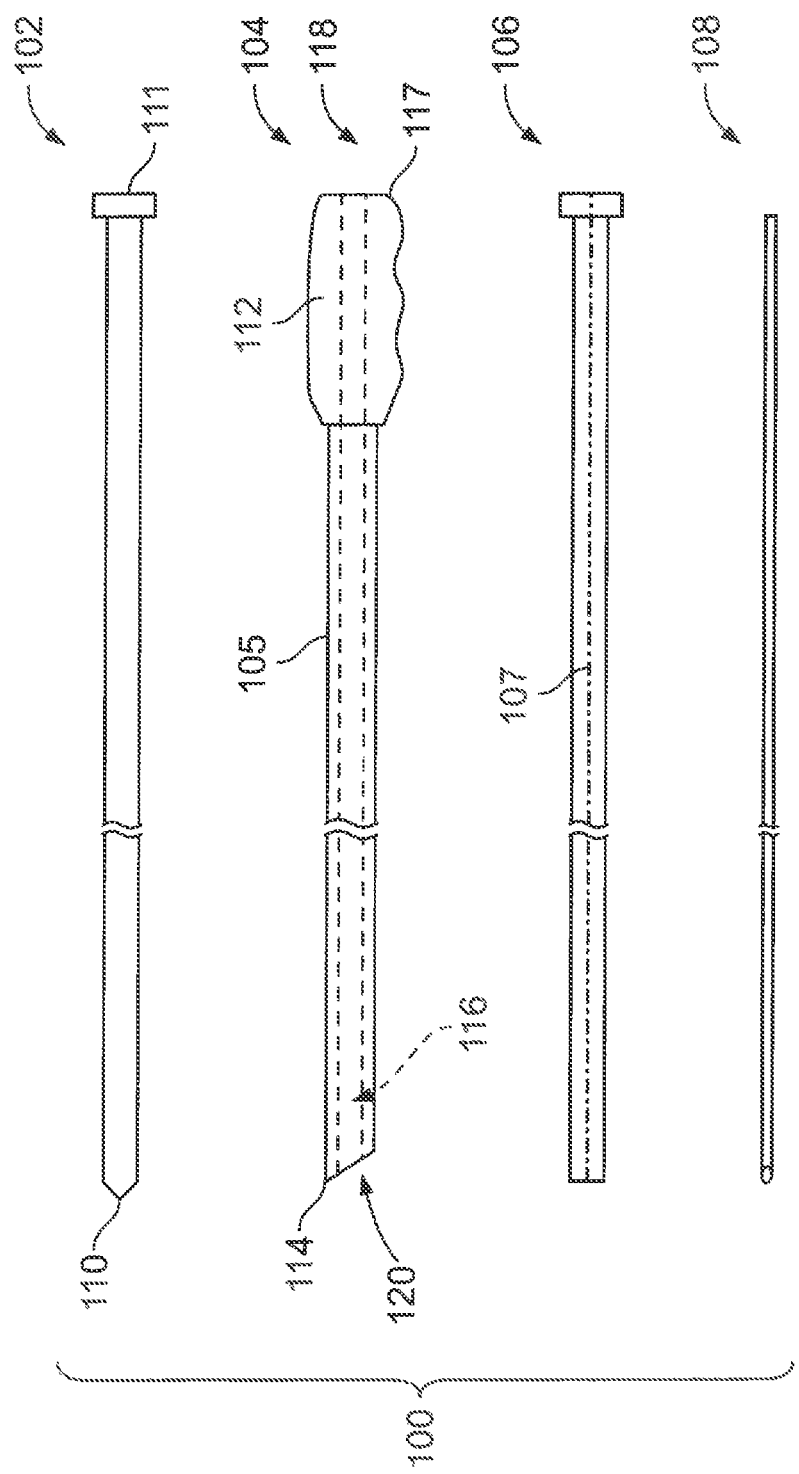
FIG. 3 illustrates different components of a delivery system that may be used for implanting the medical system of FIG. 1 in accordance with an embodiment.

FIG. 3 illustrates components of a delivery system 100 that may be used for implanting the medical system 12 (FIG. 1). In particular, the delivery system 100 may be used to create a tunnel within the patient and position a lead within the tunnel. To this end, the delivery system may include a plurality of elongated components, such as shafts, tubes, wires, and the like. The components may have inner passages or lumens that receive other components. The delivery system 100 may be a kit that includes components for multiple steps in the tunnel preparation and lead placement operations. During some operations, one or more of the components may not be utilized.

In the illustrated embodiment, the delivery system 100 includes a dissector 102, an elongated tunneling tool 104, a removable sheath 106, and a lead guide 108. The lead guide 108 may be a guide wire or a stylet. Although only a single tunneling tool 104 is shown, the delivery system or kit 100 may include one or more types of shafts and/or multiple shafts with different lengths. In some embodiments, the dissector 102 and the tunneling tool 104 may be combined and constitute a single component or only the tunneling tool 104 is used for dissecting tissue. In some embodiments, the dissector 102 may also function as a stopper or plug that prevents material from entering a lumen 116 of the tunneling tool 104.

The dissector 102 has a distal tunneling end 110 and a proximal loading end 111. The tunneling end 110 is configured to displace subcutaneous tissue and/or separate the subcutaneous tissue from other tissue layers (e.g., deep fascia layer) to form a tunnel along a designated path. The tunneling end 110 may be blunt or include portions that are sharpened. Optionally, the tunneling end 110 may include active components that may facilitate forming the tunnel. For example, the active component may be an ultrasonic device. The dissector 102 may be malleable but sufficient rigidly for displacing tissue and/or separating tissues.

The tunneling tool 104 includes an elongated shaft 105. The tunneling tool 104 has a leading end 114 that includes an opening 120 and a trailing end 117 that includes a loading port 118. A length of the tunneling tool 104 extends between the leading and trailing ends 114, 117 and may be sufficiently sized for providing the designated tunnel. The tunneling tool 104 has an operator handle 112 for directing the tunneling tool 104 during tunnel preparation and lead placement. The tunneling tool 104 has at least one lumen 116 that extends from the loading port 118 in the operator handle 112 to the leading end 114 where the opening 120 is provided. The leading end 114 may be shaped to facilitate displacing tissue. Optionally, the leading end 114 may include active elements (e.g., ultrasonic device, telemetry device, imaging device, etc.). Optionally, a portion or segment of the tunneling tool 104 may be steerable.

The tunneling tool 104 comprises a biocompatible material and may have a predetermined shape based on an anatomy of the patient. The predetermined shape may be made during manufacturing. Optionally, the tunneling tool 104 may include a malleable material such that the tunneling tool 104 may be shaped after manufacturing but prior to insertion. For instance, the tunneling tool 104 may comprise medical grade stainless steel. The tunneling tool 104 may be shaped (e.g., during manufacture or after manufacture but prior to surgery) based on a path that will be taken by the tunneling tool 104 during the tunneling process. For example, the tunneling tool 104 may be shaped for curving about the chest to the posterior location, or the tunneling tool 104 may be shaped to move along a path from the subcutaneous pocket to the sternum. The path is a function of an anatomical contour or shape of the patient's body along the corresponding path.

In the illustrated embodiment, the removable, sheath 106 is a splittable along a length of the removable sheath 106. The dashed line 107 in FIG. 3 represents where the removable sheath 106 may be separated. The removable sheath 106 may be perforated or otherwise weakened along the dashed line 107 to facilitate splitting the removable sheath 106 in a designated manner. As described below, the lead guide 108 interacts with the lead for positioning a lead at a designated location.

Figure 4:
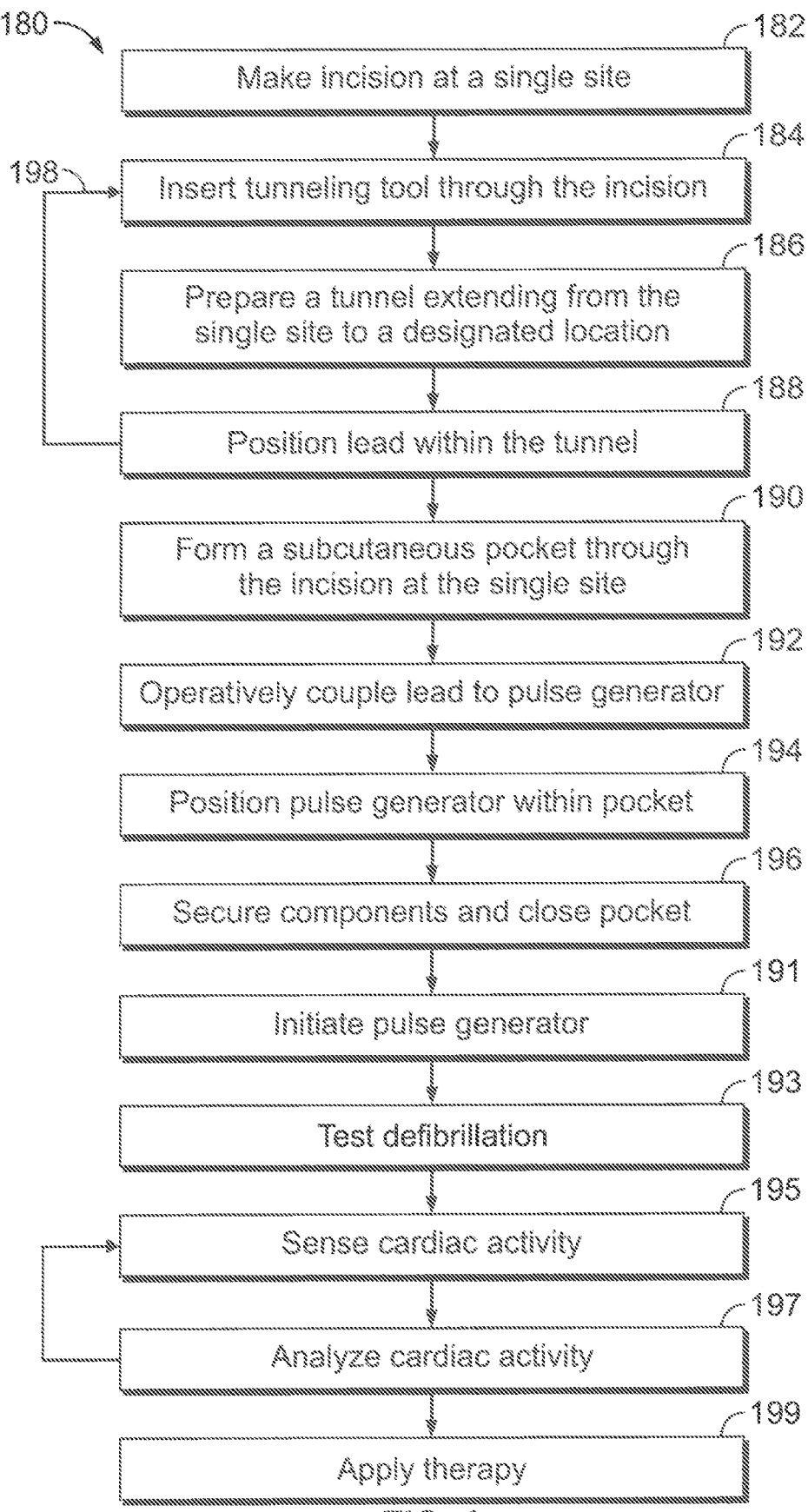
FIG. 4 is a flow chart for implanting the medical system of FIG. 1 in accordance with an embodiment.
Figure 5:
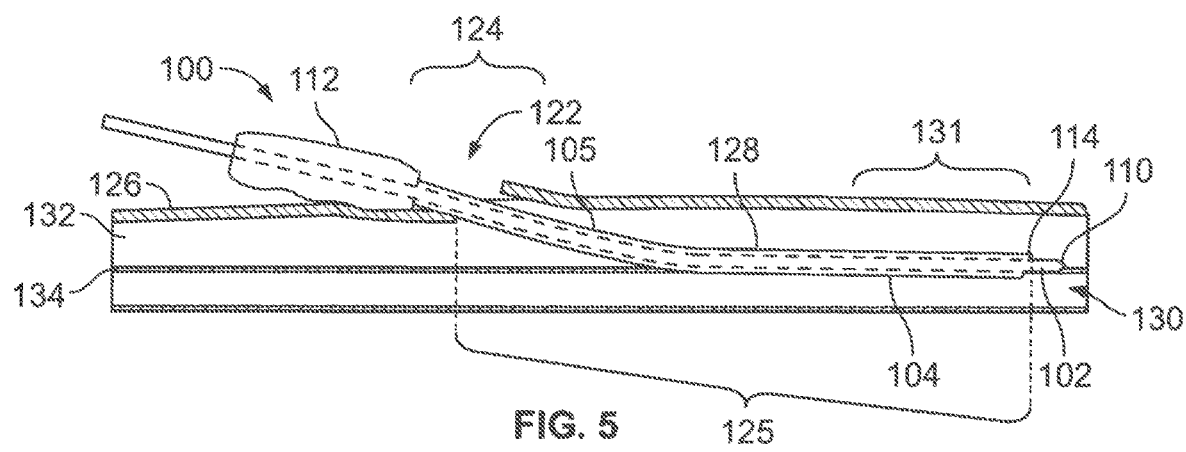
FIG. 5 is an anatomical cross-section that illustrates a tunneling operation using the delivery system of FIG. 3.

FIG. 4 illustrates a method 180 for implanting a medical system, such as the implantable medical system 12 (FIG. 1), using the delivery system 100 (FIG. 3). The method 180 is described with reference to FIGS. 5-7. The method 180 may be applicable for abdominal pockets, pre-pectoral pockets, or other pockets within the patient body. With reference to FIG. 5, the method 180 includes making, at 182, an incision 122 at a single site 124 of a patient body 126. The incision 122 may be held open using forceps (not shown). Optionally, the single site 124 may receive more than one incision to provide a larger access point to the underlying tissue. For example, a first incision may be made through the skin followed by a second incision that intersects the first incision.

At 184, the tunneling tool 104 of the delivery system 100 is inserted through the incision 122 at the single site 124. In some embodiments, the removable sheath 106 may surround the tunneling tool 104 during insertion. Optionally, the removable sheath 106 may be advanced along the tunneling tool 104 after insertion. At 186, a tunnel 128 within the underlying tissue is prepared. More specifically, the tunneling tool 104 is advanced along a path 125 through tissue of the patient until a distal end 130 of the delivery system 100 is positioned proximate to a designated location 131 (e.g., a subcutaneous posterior location or a subcutaneous parasternal location). As used herein, the "distal end of the delivery system" is the end of the component of the delivery system that leads (or is in front of) other components of the delivery system. The distal end may change based on the component being used. For example, the distal end 130 may include the tunneling end 110 of the dissector 102, the leading end 114 of the tunneling tool 104, or both when the tunneling and leading ends 110, 114 are essentially even.

The designated location 131 may be the desired location for placing an electrode or may be a location that is proximate to the desired location. A user may grip the operator handle 112, the elongated shaft 105, and/or the dissector 102 and drive the distal end 130 along the designated path 125. As the distal end 130 of the delivery system 100 moves along the path 125, the distal end 130 displaces and/or separates layers of tissues. Prior to insertion or during the tunneling operation, the tunneling tool 104 and the dissector 102 may be shaped to conform to the path 125. Alternatively or in addition to having a predetermined shape, the tunneling tool 104 and/or the dissector 102 may be steered as the distal end 130 moves through the tissue.

In the illustrated embodiment, the dissector 102 of the delivery system 100 leads the tunneling tool 104 along the path 125. The tunneling end 110 of the dissector 102 displaces tissue (e.g., subcutaneous tissue 132) and/or separates the subcutaneous tissue 132 from an underlying deep fascia layer 134. In other embodiments, the dissector 102 of the delivery system 100 is even or flush with respect to the leading end 114 of the tunneling tool 104 as the tunneling tool 104 is advanced below the skin. In such instances, the leading end 114 displaces tissue and/or separates the subcutaneous tissue 172 from an underlying deep fascia layer 174.

After the tunnel 128 is prepared, the tunneling tool 104 and the dissector 102 may be withdrawn from the tunnel 128. In some embodiments, the removable sheath 106 may remain within the underlying tissue to maintain the tunnel 128. As such, the tunneling tool 104 is withdrawn from the removable sheath 106.

Figure 6:
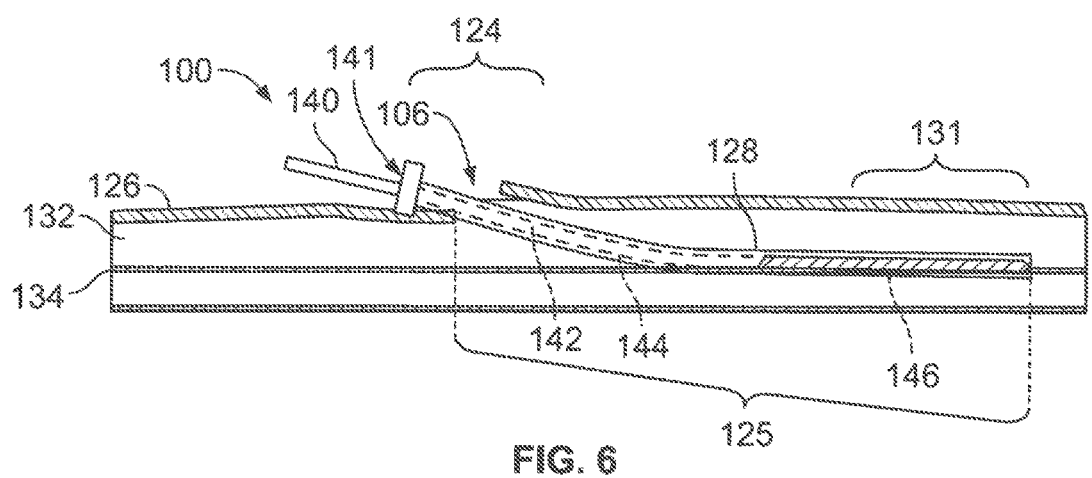
FIG. 6 is an anatomical cross-section that illustrates positioning a lead in accordance with an embodiment using the delivery system of FIG. 3.

With respect to FIG. 6, a lead 140 may be positioned, at 188, within the tunnel 128. More specifically, the lead 140 is inserted through a port of the delivery system 100. In the illustrated embodiment, the removable sheath 106 remains. The lead 140 is inserted through a port 141 and advanced through the tunnel 128 maintained by the removable sheath 106. The lead guide 108 (FIG. 3) may be used to move the lead 140. In some embodiments, the lead guide 108 is a stylet and the lead 140 includes a lumen (not shown) that is sized and shaped to receive the stylet. For example, an end of the stylet engages an interior surface of the lead 140 at an end of the lumen and pushes the lead 140 to the designated location 131.

In other embodiments, the lead guide 108 may be a guide wire. The lead 140 may include a lumen that extends entirely through the lead 140. Prior to inserting the lead 140, the guide wire may be advanced through the tunnel 128 such that a distal end of the guide wire is proximate to the designated location 131. With the guide wire positioned, a proximal end of the guide wire may be inserted into the lumen of the lead 140, and the lead 140 may be advanced through the tunnel 128 using the guide wire to direct the lead 140. Yet in other embodiments, the lead 140 may be advanced through the tunnel 128 without the use of a guide wire.

Optionally, positioning the lead 140, at 188, may be facilitated by imaging and/or tracking systems. For example, the lead 140 may be configured to communicate telemetry signals that indicate where the electrode 146 is located within the patient. Alternatively or in addition to the telemetry system, an imaging system (e.g., fluoroscopy) may be used to identify where the electrode 146 is located within the patient.

The lead 140 includes a lead body 142 having at least one inactive segment 144 and at least one electrode 146. In the illustrated embodiment, the electrode 146 is a coil electrode, but it is contemplated that other electrodes may be used. For example, the electrode 146 may be an array of electrodes. The electrode 146 is a shock electrode. Optionally, sensing electrodes may be positioned adjacent to the electrode 146 or other portions of the lead body 142.

After the lead 140 is positioned within the tunnel 128 and the electrode 146 is located at the designated position 131, the removable sheath 106 may be removed. For example, the removable sheath 106 may be split along its length as the removable sheath 106 is withdrawn from the tunnel 128. As the tunnel 128 is withdrawn, the subcutaneous tissue 132 may collapse upon the lead 140.

Lead placement may then be repeated, at 198. More specifically, a different tunnel may be prepared by inserting the delivery system 100 through the same incision at the single site 124. The delivery system 100 may utilize the same or different components. For example, a different tunneling tool and a different dissector may be used to prepare the second tunnel. In a similar manner as described above, another lead 150 (shown in FIG. 7) may be positioned within the second tunnel.

Figure 7:
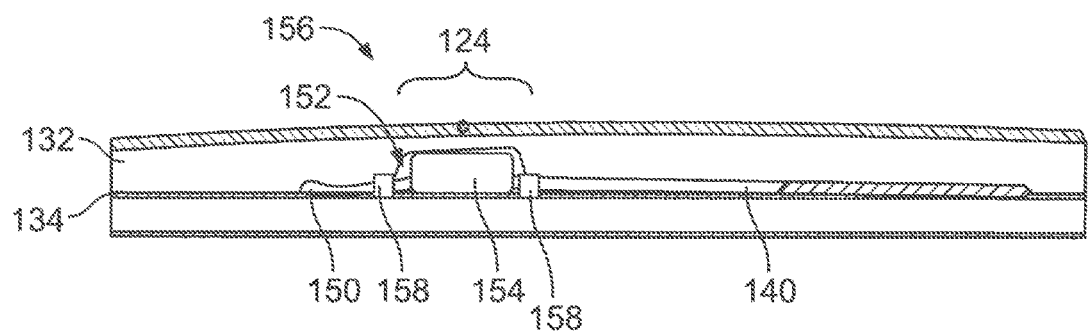
FIG. 7 is an anatomical cross-section that shows a fully implanted medical system in accordance with an embodiment.

With respect to FIG. 7, a subcutaneous pocket 152 may be formed, at 190 (FIG. 4), through the incision at the single site 124. The subcutaneous pocket 152 may be formed by displacing and/or removing portions of the subcutaneous tissue 132. It should be understood, however, that the subcutaneous pocket 152 is not required to be formed as a separate step and/or after lead positioning. The subcutaneous pocket 152 may be formed in stages and/or at different times during the method 180. For example, the subcutaneous pocket 152 may be formed after positioning the multiple leads, after positioning only one or some of the leads, or prior to positioning the leads.

At 192, the leads 140, 150 may be operatively coupled to a pulse generator 154. For example, the leads 140, 150 may have terminals (not shown) at proximal ends of the leads 140, 150 that are inserted into ports (not shown) of the pulse generator 154, thereby completing assembly of an implantable medical system 156. The implantable medical system 156 may be tested to determine if the system is operating properly.

At 194, the pulse generator 154 may be positioned within the subcutaneous pocket 152. At 196, the pulse generator 154 and the leads 140, 150 may be immobilized within the patient to reduce the likelihood that the leads 140, 150 or the pulse generator 154 may migrate. For example, the leads 140, 150 may be anchored to the deep fascia 134 using suture sleeves 158. In some embodiments, the suture sleeves 158 and attachment to the pulse generator 154 are the only anchoring mechanisms used to immobilize the leads 140, 150 within the patient. Optionally, the pulse generator 154 may also be anchored to the deep fascia 134. After immobilizing the implantable medical system 156, the incision 122 at the single site 124 may be closed.

In particular embodiments, the single site 124 is the only site where an incision is made for positioning the lead 140, for positioning the lead 150, and for positioning the pulse generator 154. As such, a medical system may be subcutaneously implanted using only a single site and, possibly, making only a single incision. In other embodiments, however, an incision may be made to facilitate positioning one or more leads. For example, for some patients, another incision at a separate site may be made to position the posterior electrode.

The method may also include initiating the pulse generator, at 191. For example, an external device (e.g., programmer) may be communicatively coupled to the pulse generator. The pulse generator may communicate identification data to the pulse generator (e.g., obtain model and serial number). The external device may generate a chart that correlates to the patient having the pulse generator. The external device may instruct the pulse generator to perform an electrode integrity check and measure parameters of the electrodes (e.g., impedance of shock electrode(s)). The external device and/or the pulse generator may determine a sensing configuration for the pulse generator based on cardiac activity. During initiation of the pulse generator, at 191, therapy parameters may be selected by the user.

Optionally, the pulse generator may be implemented with the hardware, firmware and other components of one or more of implantable medical devices (IMDs) that include neurostimulator devices, implantable leadless monitoring and/or therapy devices, and/or alternative implantable medical devices, although implemented as a subcutaneous implantable medical device. For example, the SIMD may represent a cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure in An implantable Medical Device" and U.S. Pat. No. 9,232,485 "System And Method For Selectively Communicating With An Implantable Medical Device", which are all hereby incorporated by reference in their entireties.

At 193, a defibrillation test may be performed to determine a defibrillation threshold. The test may be administered prior to or after closing the incision. The defibrillation threshold is a quantitative estimate of the ability of the heart to defibrillate. The defibrillation threshold is typically defined as the minimum shock strength that causes defibrillation. The defibrillation threshold can be measured by changing the voltages in subsequent VF inductions in accordance with a predetermined protocol. For example, the stored voltages may be incrementally decreased for subsequent VF inductions until the first shock is unable to defibrillate. This may be referred to as a step-down to failure test. If a high defibrillation threshold is identified, it may be desirable to make adjustments to the system. For example, the leads could be repositioned, the leads could be switched-out, portions of the electrodes could be capped, or another lead may be added. The defibrillation testing may be performed using an external device (e.g., programmer) that is communicatively coupled to the pulse generator.

Another defibrillation test may including applying the same energy twice. The first electrical shock may be programmed to deliver an amplitude that is less than 10 Joules from the maximum capacity of the system. To verify the effectiveness of the shock, the same amplitude may then be applied a second time. At least three to five minutes may separate subsequent applications to allow hemodynamic recovery and to minimize the cumulative effect of the electrical shocks. If the electrical shock delivered by the implantable defibrillator is ineffective, a rescue shock can be delivered either by an external defibrillator or through the implanted defibrillator.

After closing the incisions, the method may also include sensing cardiac activity at 195 and analyzing, at 197, the cardiac activity to determine whether a cardiac event-of-interest has occurred. In response to determining that a cardiac event-of-interest has occurred, a therapy may be applied, at 199. For example, the pulse generator may sense subcutaneous signals (e.g., subcutaneous ECG signals) and a cardiac, rhythm using a combination of the electrodes. The pulse generator may process the cardiac signals (e.g., filter and/or amplify) and analyze the cardiac activity to determine whether an event that requires therapy is occurring. If the pulse generator determines that a cardiac event-of-interest is occurring, such as ventricular fibrillation, ventricular tachycardia, or other arrhythmia, the pulse generator may apply therapy (e.g., electrical shock) to the heart using a combination of the electrodes.

Although FIGS. 3-7 describe certain embodiments for implanting leads using the delivery system 100, it should be understood that other delivery systems may be used, and that one or more operations (or steps) of the method 180 may be modified, replaced, or performed in different stages or at different times. One or more operations may also be added.

FIGS. 8 and 9 are an anterior view and a lateral view, respectively, of a human thoracic cage that illustrates an electrode configuration of an implantable medical system (IMD) 200 in accordance with an embodiment. For reference, the heart is also shown. More specifically, FIGS. 8 and 9 illustrate relative positions of a pulse generator 202 within a pectoral region 203, a parasternal electrode 204, and a posterior electrode 206. The IMD 200 may be implanted using the method of FIG. 4 and using a delivery system, such as the delivery system 100 (FIG. 3).

For example, an incision (not shown) may be made within the pectoral region 203 at a single site 210 located at an anterior of a chest of the patient. A first tunneling tool may be inserted through the incision at the single site 210. The tunneling tool may have, for example, an elongated shaft and a removable sheath that surrounds the elongated shaft. The tunneling tool may displace underlying tissue along a designated path to prepare a first tunnel. The first tunnel extends from the single site 210, over a plurality of intercostal gaps 212 (FIG. 9) of the chest, and within one of intercostal gaps 212 to a subcutaneous posterior location 214 (FIG. 9).

After the first tunnel is formed, the elongated shaft may be withdrawn such that the removable sheath remains within the first tunnel and maintains the first tunnel. A first lead 216 may then be positioned within the first tunnel. The first lead 216 has the posterior electrode 206 (e.g., coil electrode) at a distal portion thereof. The removable sheath may then be withdrawn allowing the subcutaneous tissue to collapse around the first lead 216.

As shown, the first lead 216 may wrap about the chest or torso of the patient. The electrode 206 may be positioned proximate to a scapula (not shown) of the patient. For example, the distal end of the electrode 206 may be positioned within an intercostal gap 212 and proximate to the tip or the inferior angle of the scapula. Transverse plane P1 intersects the apex. Transverse plane P2 intersects an upper portion of the heart, such as the atria. At least a portion of the electrode 206 may be positioned at or below the apex of the heart. For example, at least a majority of the electrode 206 may be positioned at or below the apex of the heart. The electrode 204 extends between the transverse planes P1 and P2. The electrode 204 may extend from the transverse plane P2. The transverse planes P1 and P2 and placement of the electrodes 204, 206 are based upon the size, shape, and location of the heart within the patient's body.

The electrode 206 may be at least partially positioned between a midaxillary line and a posterior axillary line of the patient. In some instances, a proximal end of the electrode 206 may be positioned beyond the midaxillary line or, possibly, the posterior axillary line of the patient. The midaxillary line is a coronal line extending along a surface of the body passing through an apex of the axilla. The posterior axillary line is a coronal line extending parallel to the midaxillary line and through the posterior axillary skinfold.

A second tunnel extending from the same single site 210 may also be prepared. The second tunnel may be prepared after the first tunnel or before the first tunnel. More specifically, a second tunneling tool may be inserted through the incision at the single site 210. The second tunneling tool has an elongated shaft and a removable sheath that surrounds the elongated shaft of the second tunneling tool. The second tunneling tool may displace underlying tissue along a designated path to prepare the second tunnel. The second tunnel extends from the single site 210 to a subcutaneous parasternal location 218. As described above, the elongated shaft may be withdrawn such that the removable sheath of the second tunneling tool maintains the second tunnel. A second lead 220 having the parasternal electrode 204 may be positioned within the second tunnel. The removable sheath may then be withdrawn allowing the subcutaneous tissue to collapse around the second lead 220. As shown, the electrode 204 is positioned parasternally (e.g., within one to three centimeters from the sternum). An end of the electrode 204 may be located proximate to the xiphoid process. As shown, the electrode 204 may extend from a point at or above the transverse plane P2 to a point at or below the transverse plane P1. A majority of the electrode 206 may be at or below the transverse plane P1. In some embodiments, at least 75% of the electrode 206 is at or below the transverse plane P1. In certain embodiments, at least 85% of the electrode 206 is at or below the transverse plane P1. In certain embodiments, at least 95% of the electrode 206 is at or below the transverse plane P1.

A subcutaneous pre-pectoral pocket may be formed prior to, during, or after the preparation of the first and second tunnels. The pulse generator 202 may be positioned within the subcutaneous pre-pectoral pocket and operatively coupled to the first and second leads 216, 220.

In the illustrated embodiment, the parasternal electrode 204 and the pulse generator 202 have the same polarity while the system provides electrical energy for defibrillation. As shown by the arrows in FIG. 9, the shock vector is directed from the parasternal electrode 204 and the pulse generator 202 to the posterior electrode 206.

Figure 11:
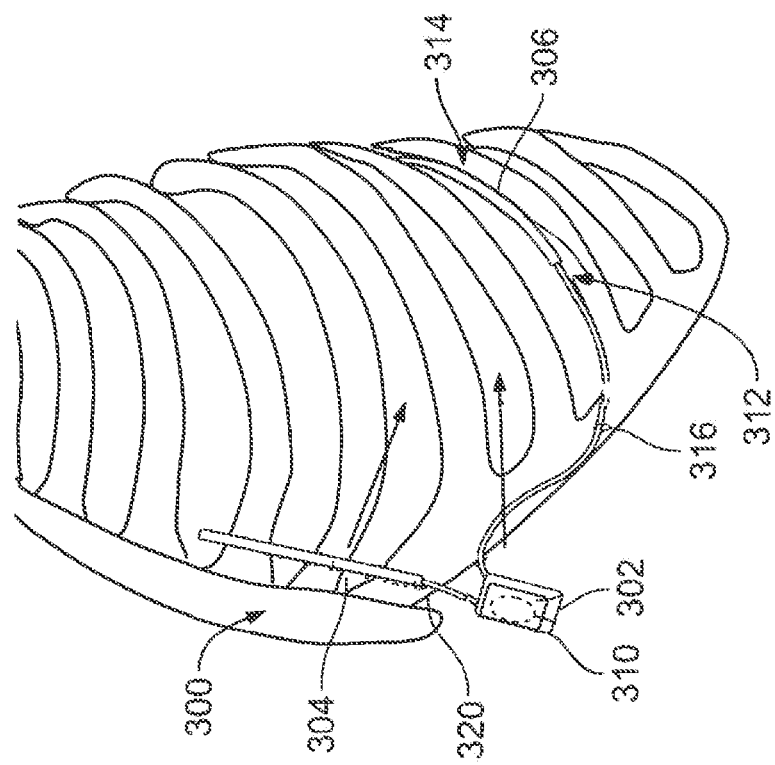
FIG. 11 is a lateral view of the thoracic cage of FIG. 10 illustrating the relative positions of the pulse generator, the parasternal electrode, and the posterior electrode coil.
Figure 10:
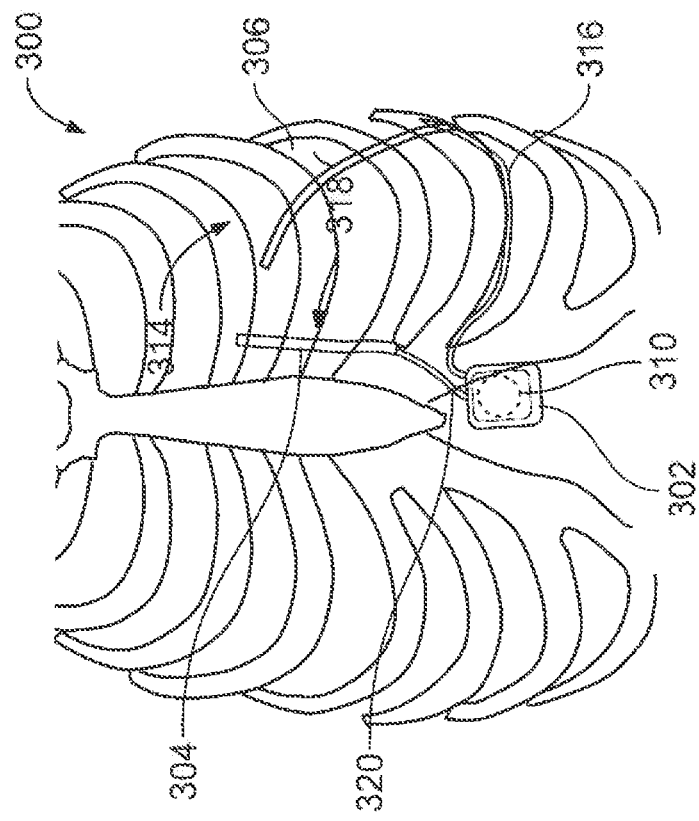
FIG. 10 is anterior view of a human thoracic cage that illustrates relative positions of a pulse generator within an abdominal region, a parasternal electrode, and a posterior electrode.

FIGS. 10 and 11 are an anterior view and a lateral view, respectively, of a human thoracic cage that illustrates an electrode configuration of an implantable medical system (IMD) 300 in accordance with an embodiment. Relative positions of a pulse generator 302 within an abdominal region 303, a parasternal electrode 304, and a posterior electrode 306. The IMD 300 may be implanted using the method of FIG. 4.

For example, an incision (not shown) may be made within the abdominal region 303 at a single site 310 in the abdomen of the patient. A first tunneling tool may be inserted through the incision at the single site 310. The tunneling tool may have, for example, an elongated shaft and a removable sheath that surrounds the elongated shaft. The tunneling tool may displace underlying tissue along a designated path to prepare a first tunnel. The first tunnel extends from the single site 310 along and through an intercostal gap 312 to a subcutaneous posterior location 314.

After the first tunnel is formed, the elongated shaft may be withdrawn such that the removable sheath remains within the first tunnel and maintains the first tunnel. A first lead 316 may then be positioned within the first tunnel. The first lead 316 has the posterior electrode 306 at a distal portion thereof. Similar to the first lead 216 (FIGS. 8 and 9), the first lead 316 may wrap about the chest or torso of the patient and be positioned proximate to the tip or the inferior angle of the scapula.

In FIGS. 10 and 11, the posterior electrode 306 is a coil electrode. Alternatively, the posterior electrode may be a patch electrode 406 (shown in FIG. 12). Returning to FIGS. 10 and 11, the removable sheath may then be withdrawn allowing the subcutaneous tissue to collapse around the first lead 316.

A second tunnel extending from the same single site 310 may also be prepared. The second tunnel may be prepared after the first tunnel or before the first tunnel. More specifically, a second tunneling tool may be inserted through the incision at the single site 310. The second tunneling tool has an elongated shaft and a removable sheath that surrounds the elongated shaft of the second tunneling tool. The second tunneling tool may displace underlying tissue along a designated path to prepare the second tunnel. The second tunnel extends from the single site 310 to a subcutaneous parasternal location 318. The second tunneling tool may move in a superior direction from the single site 310 to the subcutaneous parasternal location 318.

As described above, only the elongated shaft may be withdrawn such that the removable sheath of the second tunneling tool maintains the second tunnel. A second lead 320 having the parasternal electrode 304 may be positioned within the second tunnel. The removable sheath may then be withdrawn allowing the subcutaneous tissue to collapse around the second lead 320. As shown, the electrode 304 is positioned parasternally (e.g., within one to three centimeters from the sternum). An end of the electrode 304 may be located proximate to the xiphoid process.

A subcutaneous abdominal pocket may be formed prior to, during, or after the preparation of the first and second tunnels. The pulse generator 302 may be positioned within the subcutaneous abdominal pocket and operatively coupled to the first and second leads 316, 320.

In the illustrated embodiment, the parasternal electrode 304 and the pulse generator 302 have the same polarity while the system provides electrical energy for defibrillation. As shown by the arrows in FIG. 11, the shock vector is directed from the parasternal electrode 304 and the pulse generator 302 to the posterior electrode 306.

Figure 12:
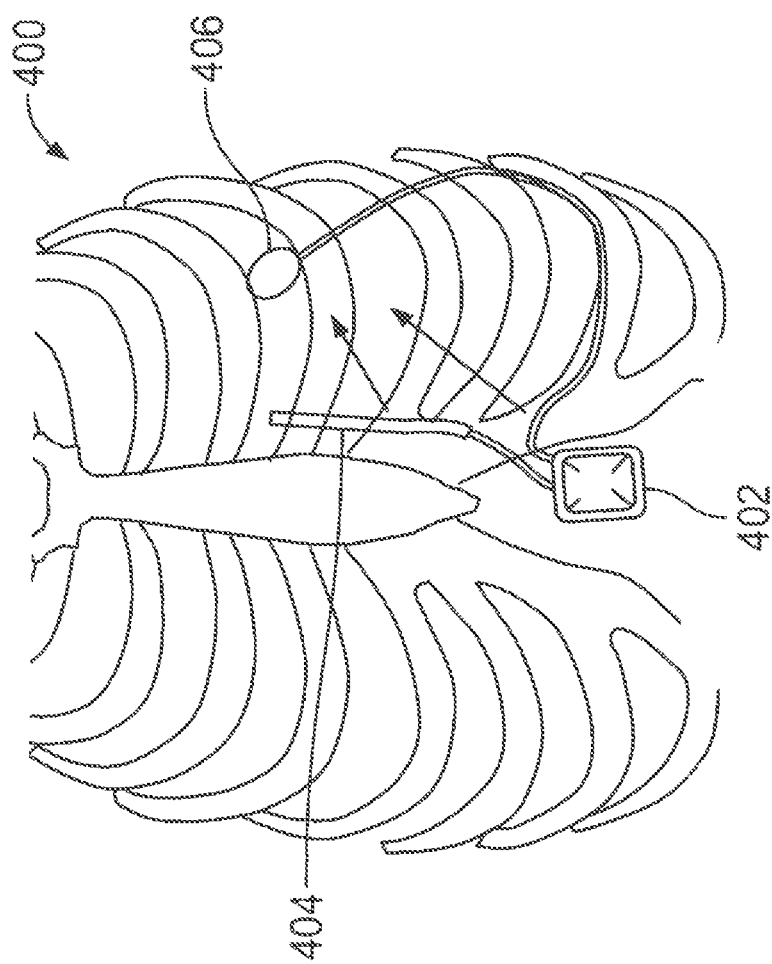
FIG. 12 is anterior view of a human thoracic cage that illustrates relative positions of a pulse generator within an abdominal region, a parasternal electrode coil, and a posterior patch electrode.

With respect to FIG. 12, the parasternal electrode 404 and the pulse generator 402 have the same polarity while the system provides electrical energy for defibrillation. As shown by the arrows in FIG. 11, the shock vector is directed from the parasternal electrode 404 and the pulse generator 402 to the posterior patch electrode 406.

Figure 13:
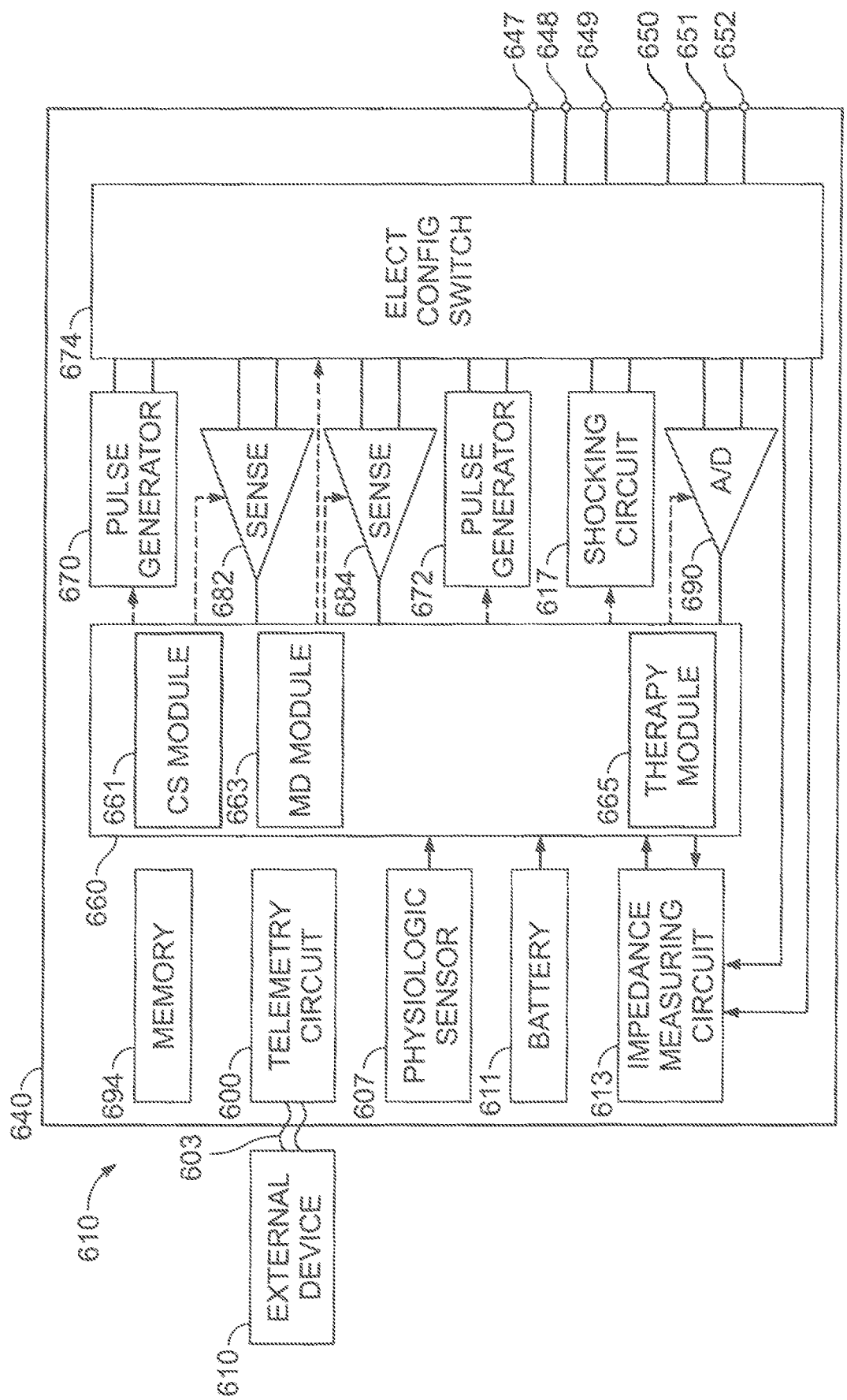
FIG. 13 illustrates a block diagram of an SIMD in accordance with an embodiment that is capable of performing stimulation therapy, including cardioversion, defibrillation, and pacing stimulation.

FIG. 13 illustrates a block diagram of an SIMD. The SIMD is capable of performing stimulation therapy, including cardioversion, defibrillation, and pacing stimulation. The SIMD is hereinafter referred to as the device 610. While a particular multi-element device is shown, this is for illustration purposes only. It is understood that the appropriate circuitry could be duplicated, eliminated or disabled in any desired combination to provide a device capable of monitoring impedance and/or cardiac signals, and/or treating the appropriate chamber(s) with cardioversion, defibrillation and pacing stimulation.

The housing 640 for the stimulation device 610 is often referred to as the "canister," "can," "case," or "case electrode" and may be programmably selected to act as the shock electrode and/or as a return electrode for some or all sensing modes. The housing 640 may further be used as a return electrode alone or in combination with one or more other electrodes. The housing 640 further includes a connector (not shown) having a plurality of terminals 647-652. To achieve sensing, pacing, and shocking in connection with desired chambers of the heart, the terminals 647-652 are selectively connected to corresponding combinations of electrodes.

The device 610 includes a programmable microcontroller 660 that controls the various modes of sensing and stimulation therapy. The microcontroller 660 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The micro controller 660 includes the ability to process or monitor input signals (data) as controlled by a program code stored in memory. The details of the design and operation of the microcontroller 660 are not critical to the present invention. Rather, any suitable microcontroller 660 may be used.

The microcontroller 660 includes inputs that are configured to collect cardiac signals associated with electrical or mechanical behavior of a heart over at least one cardiac cycle. The cardiac signals may be from the cardiac sensing circuit 682 and representative of electrical behavior of the heart. The circuit 682 may provide separate, combined, composite or difference signals to the microcontroller 660 representative of the sensed signals from the electrodes. Optionally, the cardiac signals may be the output of the A/D circuit 690 that are representative of electrical behavior of the heart. The cardiac signals may be the output of the physiologic sensor 607 that are representative of mechanical behavior.

The microcontroller 660 includes a cardiac signal (CS) module 661, a marker detection (MD) module 663 and a therapy module 665 (among other things). The CS module 661 is configured to analyze cardiac signals. The MD module 663 is configured to analyze signals sensed over the marker sensing channel and identify incoming event markers. The therapy module 665 is configured to modulate, over multiple cardiac cycles, at least one therapy parameter while the device 610 obtains a collection of at least one CSF indicators associated with different therapy parameters. The therapy module 665 is further configured to adjust a therapy configuration based on, among other things, the cardiac signals and based on the event markers.

The microcontroller 660 further controls a shocking circuit 617 by way of a control signal The shocking circuit 617 generates stimulating pulses of low (up to 0.5 Joules), moderate (0.5-10 Joules), or high energy (11 to 50 Joules), as controlled by the microcontroller 660. Stimulating pulses may be applied to the patient's heart through at least two shocking electrodes.

One or more pulse generators 670 and 672 generate various types of therapy, such as pacing and ATP stimulation pulses for delivery by desired electrodes. The electrode configuration switch 674 (also referred to as a switch bank) controls which terminals 647-652 are connected to the pulse generators 670, 672, thereby controlling which electrodes receive a therapy. The pulse generators, 670 and 672, may include dedicated, independent pulse generators, multiplexed pulse generators, shared pulse generators or a single common pulse generator. The pulse generators 670 and 672 are controlled by the microcontroller 660 via appropriate control signals to trigger or inhibit stimulation pulses. The microcontroller 660 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 674 connects the sensing electronics to the desired terminals 647-652 of corresponding sensing electrodes. For example, a portion of the terminals may be coupled to electrodes configured to define a sensing and/or shocking vector that passes through the left ventricle. The switch 674 may connect terminals to the event marker sensing circuit 684 (which corresponds to the event marker sensing channel) and the microcontroller. The circuit 684 may amplify, filter, digitize and/or otherwise process the sensed signals from the select electrodes.

The switch 674 also connects various combinations of the electrodes to an impedance measuring circuit 613. The impedance measuring circuit 613 includes inputs to collect multiple measured impedances between corresponding multiple combinations of electrodes. For example, the impedance measuring circuit 613 may collect a measured impedance for each or a subset of the active sensing vectors. Optionally, the impedance measuring circuit 613 may measure respiration or minute ventilation; measure thoracic impedance for determining shock thresholds; detects when the device has been implanted; measures stroke volume; and detect the opening of heart valves, etc.

The switch bank 674 includes a plurality of switches for connecting the desired electrodes to the appropriate I/O circuits, thereby providing complete electrode programmability. The switch 674, in response to a control signal from the microcontroller 660, determines the polarity of the stimulation pulses (e.g., unipolar, bipolar, co-bipolar, etc.) by selectively closing the appropriate combination of switches (not specifically shown). The outputs of the cardiac signal and event marker sensing circuits 682 and 684 are connected to the microcontroller 660 which, in turn, is able to trigger or inhibit the pulse generators 670 and 672, respectively. The sensing circuits 682 and 684, in turn, receive control signals from the microcontroller 660 for purposes of controlling the gain, threshold, the polarization charge removal circuitry (not shown), and the timing of any blocking circuitry (not shown).

Cardiac signals are also applied to the inputs of an analog-to-digital (A/D) data acquisition system 690. The data acquisition system 690 is configured to acquire cardiac signals, convert the raw analog data into a digital signal, and store the digital signals for later processing and/or telemetric transmission to an external device 610. The data acquisition system 690 samples cardiac signals across any pair of desired electrodes. The data acquisition system 690 may be coupled to the microcontroller 660, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 660 is further coupled to a memory 694 by a suitable data/address bus 696. The memory 694 stores programmable operating, impedance measurements, impedance derivation and therapy-related parameters used by the microcontroller 660. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 694 through a telemetry circuit 600 in telemetric communication with the external device 610, such as a programmer, trans-telephonic transceiver, or a diagnostic system analyzer. The telemetry circuit 600 is activated by the microcontroller 660 by a control signal. The telemetry circuit 600 advantageously allows data and status information relating to the operation of the device (as contained in the microcontroller 660 or memory 694) to be sent to an external device 101 through an established communication link 603.

The stimulation device 610 may include a physiologic sensor 607 to adjust pacing stimulation rate according to the exercise state of the patient. The physiological sensor 607 may further be used to detect changes in cardiac output, changes in the physiological condition of the heart, or diurnal changes in activity (e.g., detecting sleep and wake states). The battery 611 provides operating power to all of the circuits shown in FIG. 7.

It will be readily understood that the components of the embodiments as generally described and illustrated in the Figures herein, may be arranged and designed in a wide variety of different configurations in addition to the described example embodiments. Thus, the more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein," Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:

1. A method comprising:
   making an incision at a single site of a patient, the single site located at an anterior of a chest or abdomen of the patient;
   inserting a tunneling tool through the incision at the single site and preparing a first tunnel from the single site to a subcutaneous posterior location, wherein a path of the first tunnel at least one of i) extends over a plurality of intercostal gaps of the chest or ii) extends along and within one of the intercostal gaps;
   positioning a first lead having an electrode within the first tunnel;
   inserting the tunneling tool or a different tunneling tool through the incision at the single site and preparing a second tunnel from the single site to a subcutaneous parasternal location along the chest;
   positioning a second lead having an electrode within the second tunnel;
   positioning a pulse generator within a subcutaneous pocket and operatively coupling the first and second leads to the pulse generator;
   closing the single site; and
   sensing cardiac activity, wherein the pulse generator is configured to analyze the cardiac activity and provide therapy in response to identifying a cardiac event-of-interest using the cardiac activity.

2. The method of claim 1, wherein the path of the first tunnel extends beyond a posterior axillary line of the patient, the single site being the only site where an incision is made for positioning the first lead, for positioning the second lead, and for positioning the pulse generator.

3. The method of claim 2, wherein the posterior location is within a region below the inferior angle of a scapula.

4. The method of claim 1, further comprising shaping the tunneling tool or the other tunneling tool based on an anatomical shape of the patient along the corresponding path.

5. The method of claim 1, wherein the tunneling tool is surrounded by a removable sheath, wherein preparing the first tunnel includes moving the tunneling tool and the removable sheath through subcutaneous tissue to form the first tunnel and removing the tunneling tool such that the removable sheath remains within the first tunnel.

6. The method of claim 1, wherein at least one of the first lead or the second lead is anchored to deep fascia within the subcutaneous pocket at an anchor point, the anchor point being the only anchor point in which the at least one lead is anchored directly to patient.

7. The method of claim 1, wherein a volume of the pulse generator is at most 40 milliliters.

8. The method of claim 1, wherein the pulse generator is configured to generate a defibrillating energy of at most 50 Joules, the pulse generator and the electrode of the second lead having a common polarity.

9. The method of claim 1, wherein the electrode of the first lead has an active length that is at least 12 centimeters (cm) and wherein the electrode of the second lead has an active length that is at least 8 cm.

10. The method of claim 1, wherein the electrode of the first lead includes an electrode patch positioned at the posterior location, the electrode patch having an active area that is at least 30 cm$^2$.

11. The method of claim 1, wherein a volume of the pulse generator is at most 40 milliliters and is configured to generate a defibrillating energy of at most 50 Joules, the electrode of the first lead having an active length that is at least 12 cm and the electrode of the second lead having an active length that is at least 8 cm.

12. A method comprising:
making an incision at a single site of a patient, the single site located at an anterior of a chest of the patient;
inserting a first tunneling tool through the incision at the single site, the first tunneling tool having an elongated shaft and a removable sheath that surrounds the elongated shaft;
displacing underlying tissue with the first tunneling tool along a designated path to prepare a first tunnel, the first tunnel extending from the single site, over a plurality of intercostal gaps of the chest, and within one of intercostal gaps to a subcutaneous posterior location;
withdrawing the elongated shaft, the removable sheath maintaining the first tunnel;
positioning a first lead having an electrode within the first tunnel;
withdrawing the removable sheath;
inserting a second tunneling tool through the incision at the single site, the second tunneling tool having an elongated shaft and a removable sheath that surrounds the elongated shaft of the second tunneling tool;
displacing underlying tissue with the second tunneling tool along a designated path to prepare a second tunnel, the second tunnel extending from the single site to a subcutaneous parasternal location;
withdrawing the elongated shaft of the second tunneling tool, the removable sheath of the second tunneling tool maintaining the second tunnel;
positioning a second lead having an electrode within the second tunnel;
withdrawing the removable sheath of the second tunneling tool;
forming a subcutaneous pre-pectoral pocket; and
positioning a pulse generator within the subcutaneous pre-pectoral pocket and operatively coupling the first and second leads to the pulse generator.

13. The method of claim 12, wherein the path of the first tunnel extends beyond a posterior axillary line of the patient, the single site being the only site where an incision is made for positioning the first lead, for positioning the second lead, and for positioning the pulse generator.

14. The method of claim 12, further comprising shaping at least one of the elongated shafts based on an anatomical shape of the patient along the corresponding designated path.

15. The method of claim 12, wherein the pulse generator is configured to generate a defibrillating energy of at most 50 Joules, the pulse generator and the electrode of the second lead having a common polarity.

16. The method of claim 15, wherein a volume of the pulse generator is at most 40 milliliters, the electrode of the first lead having an active length that is at least 12 centimeters (cm) and the electrode of the second lead having an active length that is at least 8 cm.

17. The method of claim 12, further comprising closing the single site and sensing cardiac activity, wherein the pulse generator is configured to provide therapy in response to identifying a cardiac event-of-interest using the cardiac activity.

18. A method comprising:
making an incision at a single site of a patient, the single site located at an abdomen of the patient;
inserting a first tunneling tool through the incision at the single site, the tunneling tool having an elongated shaft and a removable sheath that surrounds the elongated shaft;
displacing underlying tissue with the tunneling tool along a designated path to prepare a first tunnel, the first tunnel extending from the single site along an intercostal gap to a subcutaneous posterior location;
withdrawing the elongated shaft, the removable sheath maintaining the first tunnel;
positioning a first lead having an electrode within the first tunnel;
withdrawing the removable sheath;
inserting a second tunneling tool through the incision at the single site, the second tunneling tool having an elongated shaft and a removable sheath that surrounds the elongated shaft of the second tunneling tool;
displacing underlying tissue with the second tunneling tool along a designated path to prepare a second tunnel, the second tunnel extending in a superior direction from the single site to a subcutaneous parasternal location;
withdrawing the elongated shaft of the second tunneling tool, the removable sheath of the second tunneling tool maintaining the second tunnel;
positioning a second lead having an electrode within the second tunnel;
withdrawing the removable sheath of the second tunneling tool;
forming a subcutaneous abdominal pocket; and
positioning a pulse generator within the abdominal pre-pectoral pocket and operatively coupling the first and second leads to the pulse generator.

19. The method of claim 17, wherein the path of the first tunnel extends beyond a posterior axillary line of the patient, the single site being the only site where an incision is made for positioning the first lead, for positioning the second lead, and for positioning the pulse generator.

20. The method of claim 17, further comprising shaping at least one of the elongated shafts based on an anatomical shape of the patient along the corresponding designated path.

21. The method of claim 17, wherein the pulse generator is configured to generate a defibrillating energy of at most 50 Joules, the pulse generator and the electrode of the second lead having a common polarity.

22. The method of claim 17, wherein the electrode of the first lead includes a patch electrode.

23. The method of claim 17, further comprising closing the single site and sensing cardiac activity, wherein the pulse generator is configured to provide therapy in response to identifying a cardiac event-of-interest using the cardiac activity.

* * * * *